United States Patent [19]
Marangoni et al.

[11] Patent Number: 5,205,734
[45] Date of Patent: Apr. 27, 1993

[54] APPARATUS FOR REMOVING CERAMIC ORTHODONTIC BRACKETS AND AN ASSOCIATED METHOD

[75] Inventors: Roy D. Marangoni; Jeffery L. Rickabaugh, both of Pittsburgh, Pa.

[73] Assignee: University of Pittsburgh of the Commonwealth System of Higher Education, Pittsburgh, Pa.

[21] Appl. No.: 824,258

[22] Filed: Jan. 21, 1992

[51] Int. Cl.$^5$ .......................... A61C 3/00; A61C 1/00
[52] U.S. Cl. .......................................... 433/4; 433/29
[58] Field of Search ................ 433/3, 4, 159, 215, 433/29

[56] References Cited

U.S. PATENT DOCUMENTS

| | | | |
|---|---|---|---|
| 4,553,932 | 1/1985 | Armstrong et al. | 433/4 |
| 4,907,965 | 3/1990 | Martin | 433/3 |
| 5,040,975 | 8/1991 | Ettwein et al. | 433/3 |
| 5,055,048 | 10/1991 | Vassiliadis et al. | 433/215 |
| 5,090,908 | 2/1992 | Teumim-Stone | 433/215 |

OTHER PUBLICATIONS

Electro Thermal Debonder Operator's Manual, "A'-'-Company, a Johnson & Johnson Company.

Primary Examiner—Gene Mancene
Assistant Examiner—Nicholas D. Lucchesi
Attorney, Agent, or Firm—Arnold B. Silverman

[57] ABSTRACT

Apparatus for removing an adhesively bonded ceramic orthodontic bracket from a tooth to which it is secured includes a body portion which has a handle and a head portion. Bracket engaging jaws are disposed within the head portion. The jaws may be opened and closed to engage and disengage the bracket. A laser generator creates a laser beam which passes through a guide tube and through a discharge end of the guide tube which is positioned in spaced relationship with respect to the bracket. An associated method is provided.

21 Claims, 3 Drawing Sheets

_5,205,734_

APPARATUS FOR REMOVING CERAMIC ORTHODONTIC BRACKETS AND AN ASSOCIATED METHOD

BACKGROUND OF THE INVENTION

1. Field of the Invention

This invention relates to apparatus and a method for removal of ceramic orthodontic dental brackets from a tooth.

2. Description of the Prior Art

It has long been known to employ orthodontic procedures as a means for establishing relative movement of teeth for therapeutic or cosmetic purposes. In general, in such systems, brackets are attached to individual teeth and archwires are secured thereto. In this manner, by establishing the desired tension within the archwire, over a period of time, the desired change and relative positioning of the teeth may be effected.

One known form of the effecting orthodontic treatment is to place adhesively secured metal brackets on the individual teeth and to secure the archwire to the metal brackets.

In many uses, particularly in respect of the increasing use of orthodontic treatment by adults, it has been desirable to make the orthodontic appliances less visible. As a result, the use of ceramic brackets in lieu of metal brackets has come into wide-spread use. Such brackets typically have a contoured surface which is secured to a front tooth surface by an appropriate adhesive such as resin, for example. The bracket has a transverse groove for receipt of the archwire which passes therethrough.

Such ceramic brackets may, for example, be made of aluminum oxides.

As orthodontic treatment progresses or is terminated, it is frequently necessary or desirable to remove the brackets. It has been known to use various sorts of manual dental appliances to pry the brackets free. Among the disadvantages of this approach are the possible infliction of pain on the patient, as well as the anxiety created and the risk that hand instrument may slip and accidentally cause injury to the patient. Also, there is the risk of removing enamel along with the bracket at the time of removal.

U.S. Pat. No. 4,553,932, the disclosure of which is incorporated herein by reference, discloses mechanical means for pulling bonded ceramic orthodontic brackets off of teeth. It provides a device which has a loop adapted to engage the bracket. A body member and a trigger member rotatable with respect thereto effects movement of the loop and removal of the bracket with counterforces being applied to the tooth adjacent to the bracket while such withdrawing forces are applied. In using this system, the two abutments may be positioned on opposed sides of the bracket in contact with the tooth, the loop may then be engaged and, through the action of movement of a trigger to effect loop withdrawing forces and the stabilizing effect of a spacer hook of a spacer tenaculum, the bracket is withdrawn as a unit. It has also been known to provide a similar device having a pair of movable cooperating jaws in lieu of the bracket engaging loop. A problem with this approach is that these systems place reliance upon the application of force which can be anxiety producing and, in some instances, injurious to the patient.

It has also been known to employ an electrically energized heating element in contact with the bracket so as to soften the adhesive and permit removal. Such device is sold under the trade designation Electro Thermal Debonder by Johnson & Johnson. One of the potential disadvantages of this approach is the risk of accidentally bringing the heated member in contact with the patient.

In spite of the foregoing new disclosures, there remains a very real and significant need for improved means of removing ceramic orthodontic brackets from a patient's mouth.

SUMMARY OF THE INVENTION

The present invention has met the need by providing noncontacting heating means for thermally freeing ceramic orthodontic brackets in an efficient and safe manner.

The apparatus of the present invention includes a body portion having a handle and head portion with bracket engaging means disposed within the head portion. Operating means are provided for opening and closing the bracket engaging means. Laser generating means generate a laser beam which is transmitted by guide means to the bracket. The guide means have a discharge opening disposed in spaced relationship with respect to the bracket. Switch means activate the laser generating means which delivers a focused laser beam of predetermined duration and intensity to the bracket. Depending upon the laser selected, the ceramic material may be transparent with respect to the laser beam which may impinge directly on the adhesive or may impinge upon the front surface of the bracket which is not transparent thereto and be thermally conducted to the adhesive or may volatilize the adhesive securing the bracket means to the tooth.

The method of the present invention includes employing laser means to generate a beam of the desired duration and intensity and causing the same to impinge upon the bracket by guide means which has a discharge end in spaced relationship with respect to the bracket. The laser beam is preferably oriented generally perpendicularly with respect to the front face of the bracket.

It is an object of the present invention to provide a rapid, safe and effective means for removing orthodontic ceramic brackets from teeth.

It is another object of the present invention to effect such removal without damage to the tooth or other portions of the patient's mouth.

It is yet another object of the present invention to provide means for automatically positioning the guide discharge end in the desired spaced relationship with respect to the bracket.

It is another object of the present invention to employ laser beams and effecting removal of the bracket while avoiding the need to expose a patient to undo anxiety.

These and other objects of the present invention will be fully understood from the following description of the invention in reference to the illustrations appended hereto.

DESCRIPTION OF THE PREFERRED EMBODIMENTS

Figure 1:
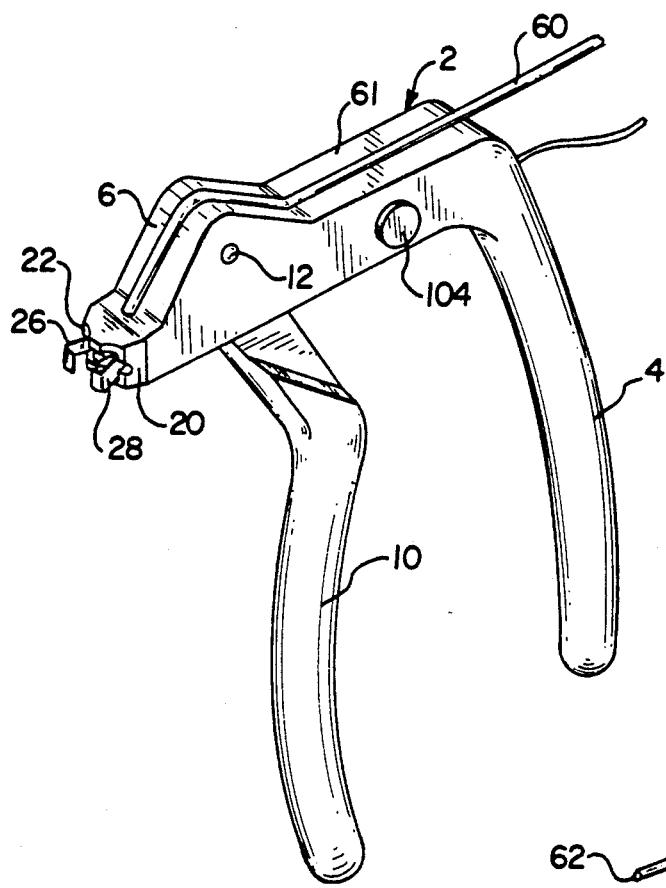
FIG. 1 is a perspective view of a form of apparatus of the present invention.
Figure 2:
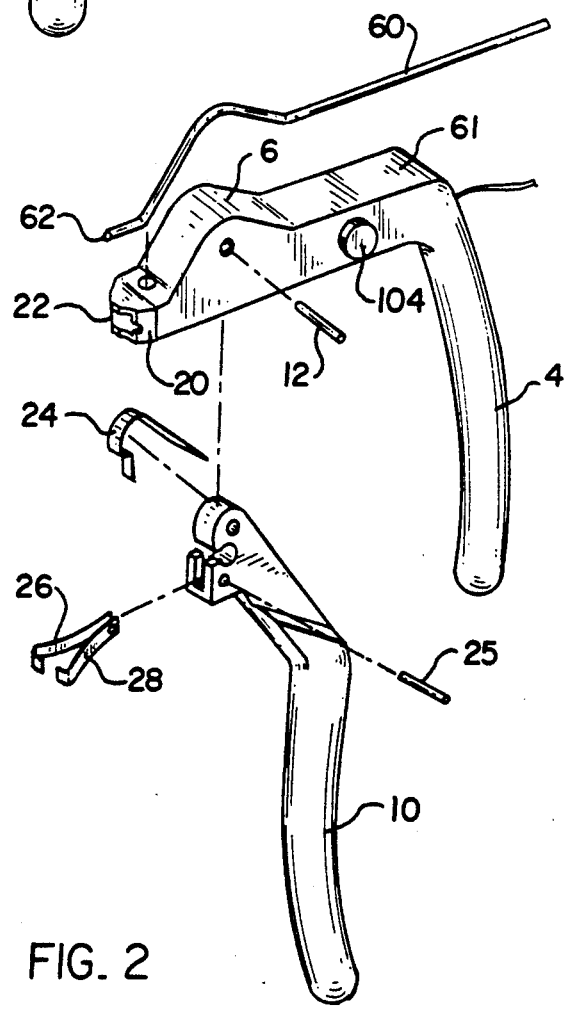
FIG. 2 is an exploded view of the apparatus of FIG. 1.

As is shown in FIGS. 1 and 2, the body 2 includes a handle portion 4 and a head portion 6. A trigger means 10 is rotatably secured to the head portion 6 by means of pivot pin 12. The free end of the head portion has a pair of projecting abutments 20, 22 which are adapted to be in contact with a tooth on opposite sides of the bracket. Movement of the trigger means 10 against the influence of spring means 24 causes the movable jaw means 26, 28, which are secured to trigger means 10 by pin 25, to be subjected to relative opening and closing movement. The jaw means 26, 28 in the open position have a greater opening than the width of the bracket in order to permit them to be moved into clamping engagement with the sides of the bracket when the jaw means 26, 28 are in the closed position.

Figure 3:
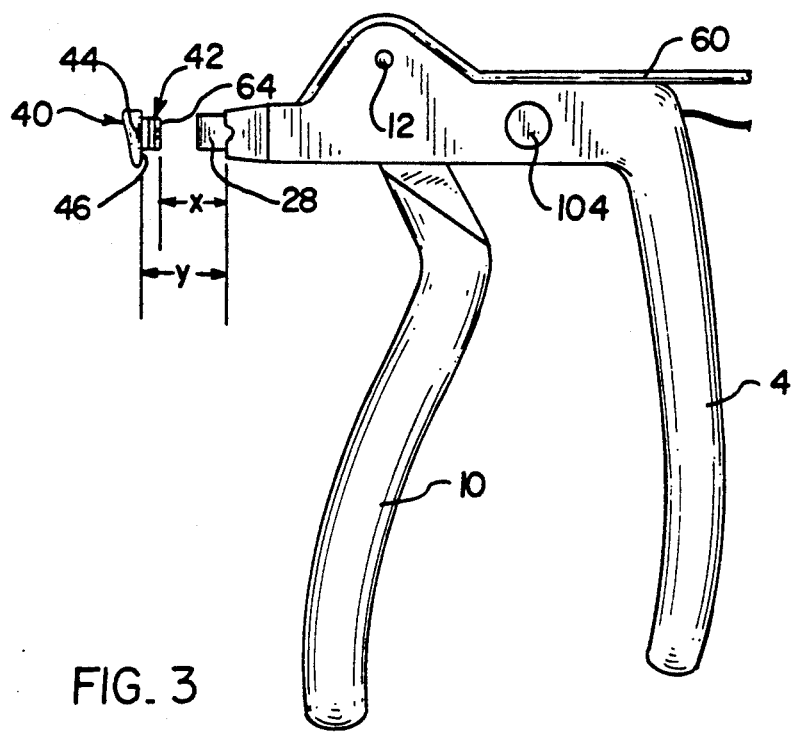
FIG. 3 is a partial cross-sectional illustration showing the apparatus of the present invention disposed adjacent to a bracket secured to a tooth.
Figure 4:
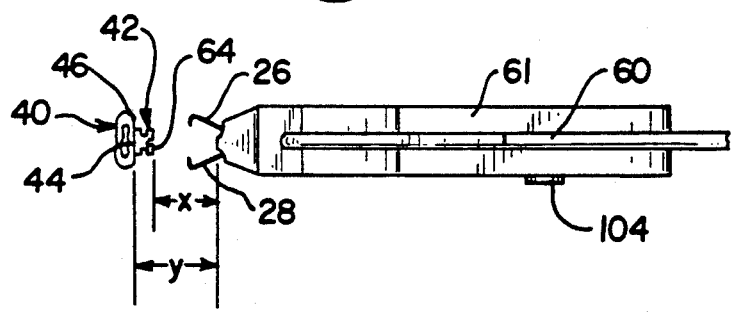
FIG. 4 is a top plan view of the bracket and tooth shown in FIG. 3.

Referring to FIG. 3 and 4, it will be seen that a tooth 40 has a bracket 42 bonded thereto, preferably by means of an interposed adhesive (not shown) such as a suitable epoxy or other resin, for example. The rear surface 44 of bracket 42 is generally of complementary shape with respect to the adjacent tooth surface and is secured to the front surface 46 of the tooth.

As shown in FIGS. 1 through 4, laser guide means 60 rests on the upper surface 61 of the head portion 6. The portion of guide means 60 close to the abutments 20, 22, extends out of head portion 6 and toward the bracket when in operating position. As shown in FIGS. 3 and 4, guide means 60 has a discharge end 62 which is preferably spaced a distance x which is about 0.5 to 3 mm from the front of the bracket 42 and a distance y of about 2 to 6 mm from the front surface 46 of the tooth 40. The laser beam which impinges substantially perpendicularly on the front surface 64 of the bracket 42 is focused in a conventional manner on the bracket by lens means (not shown) disposed within the path of laser beam travel.

It will be appreciated that in this manner there is no need to contact the bracket 42 with any portion of the apparatus of elevated temperature and, therefore, the risk of a burned patient or user of the apparatus is eliminated.

Figure 5:
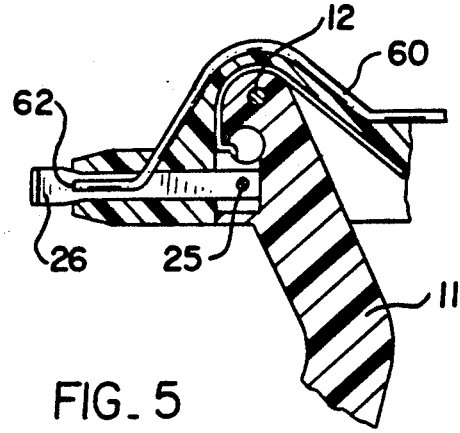
FIG. 5 is a cross sectional illustration showing a portion of the apparatus of the present invention.

FIG. 5 shows a cross-sectional illustration of the trigger means 10 in the bracket-engaging position with the guide means 60 aligned with the bracket 42.

The jaw means 26, 28 may be made of leaf spring material. As the trigger means 10 moves rearwardly, the jaw means 26, 28, move toward each other into closed position. Release of trigger means 10 causes it to rotate forwardly about pin 12 under the influence of spring 24 and thereby open jaw means 26, 28. In the preferred embodiment, the jaw means 26, 28, when closed, will move into the head portion 6 sufficiently to have the abutment means 20, 22 be in contact with the tooth 40 on opposed sides of bracket 42 to facilitate derived positioning of discharge end 62 with respect to the bracket 42 and removal of the bracket 42 of after heating.

Figure 6:
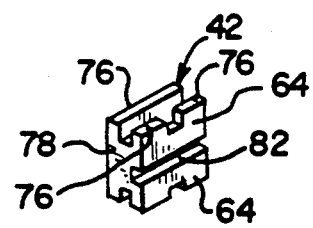
FIG. 6 is a perspective view of a form of orthodontic bracket to be removed by the apparatus method of the present invention.

Referring to FIG. 6 there shown, a form of ceramic bracket 42 which may be composed of aluminum oxide, it will be appreciated that the bracket has a segmented upper surface 76, a side surface 78, and a segmented front surface 64. The other side surface (not shown) will generally have the same configuration as side surface 78 and the bottom configuration (not shown) will generally be the same as the upper surface 76. A generally horizontally oriented forwardly open groove 82 is adapted to receive the archwire.

Figure 7:
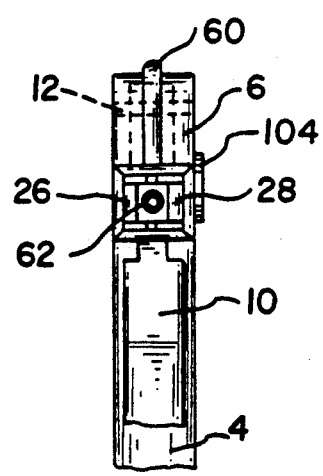
FIG. 7 is a side elevational view of the apparatus of the present invention.

As shown in FIG. 7, the head portion 6 has a pair of jaw means 26, 28 which are disposed on opposite sides of the discharge end 62 of the guide means 60. This view shows the apparatus as viewed from the bracket 42.

Figure 8:
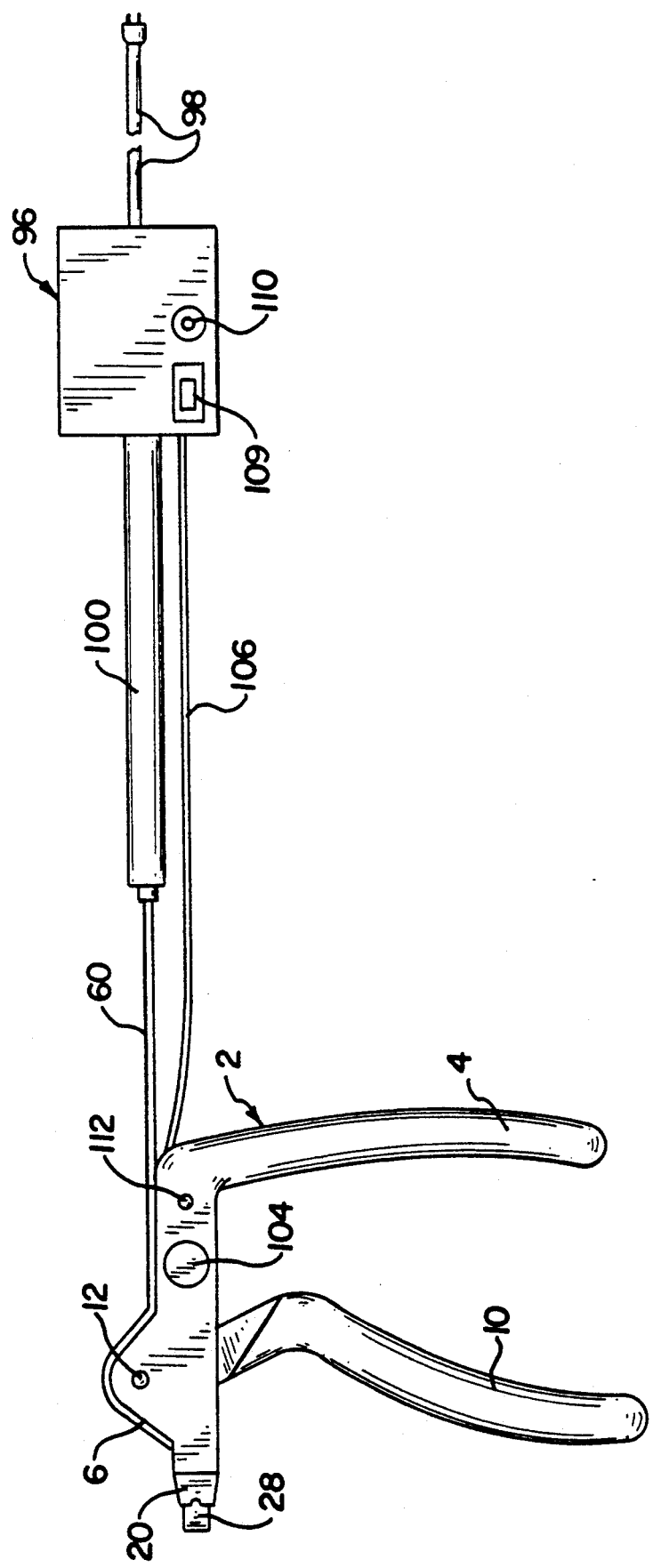
FIG. 8 is a schematic drawing of the apparatus of the present invention showing the connections between the laser generating means and the tool which removes the bracket.

Referring to FIG. 8, several additional features of the invention will be considered. The laser generating means 96 is connected to a suitable source of alternating current through wire 98. The laser may take any desired form well known to those skilled in the art, depending upon what type of laser energy is desired. For example, if it is desired to have the laser be nontransparent with respect to the ceramic bracket material, a $CO_2$ laser may be employed. In this manner, the laser energy will impinge on the front surface 64 of bracket 42 and through thermal conduction reach the adhesive and soften the same, after which the apparatus may be employed to mechanically remove the bracket 42 with the jaw means 26, 28 in the bracket engaging position. In the alternative, if it is desired to have the laser beam be relatively transparent with respect to the bracket and an excimer laser which is generally of the ultraviolet wavelength type may be employed in order to have some of the laser energy pass directly through the transparent bracket and soften the adhesive. Further, if desired, a laser may be selected so as to have sufficiently high energy as to volatilize the adhesive securing the bracket to the tooth. Generally, the laser beam will accomplish the desired heating in less than about 5 seconds. For example, a 20 watt laser may be employed with an intensity wavelength of about 10.6 micrometers for about 4 seconds. Connecting the laser generating means 96 with the guide means 60 is tubular wand 100 to thereby provide a leakproof continuous path for the laser beam from the laser generating means 96 to the guide means discharge end 62.

In order to activate the laser, switch means 104 (FIGS. 1–3 and 7–8) which may take the form of a spring biased button disposed on the body portion 2 of the apparatus may be provided with an electrical wire 106 connecting the switch means 104 with the laser generating means 96 to activate the same. Depressing of this button 104 will cause the preset laser generating means 96 to emit a laser beam of desired energy intensity and duration. It will be appreciated that by repeatedly depressing this button, additional cycles of laser beams may be generated. In general, it will be contemplated that a single beam of desired intensity, which will be well known to those skilled in the art, will generally have a duration of less than about five seconds in order to soften the adhesive of a ceramic orthodontic bracket. After that bracket has been removed, the apparatus may then be employed on the next bracket desired to be removed.

If desired, suitable safety switch means which minimize the risk of accidental depression of the switch may be employed. For example, a rotatable safety cover (not shown) may be secured to the body portion 2 and may take the form of a disk rigidly secured to a post which has its other end pivotally attached to the body portion 2 so that rotation of the disk is required before the button can be depressed. Also, if desired, opposing spring biased buttons may be positioned on opposite sides of the body portion with depression of both buttons being required before the system can be activated. Other means will be well known to those skilled in the art.

Also, various other means for positioning the activating switch may be provided, if desired. For example, in lieu of the push button switch 104 mounted on the body portion 2, a foot activated pedal switch (not shown) may be employed.

If desired, a suitable indicator light 110 may be placed on the housing of the laser generating means 96 to show that on-off switch 109 is in the "on" position and the system is "on" and a light 112 may be placed on body portion 2 to be illuminated during the period when a laser beam is being generated. These lights may be light emitting diodes, if desired.

If desired, the apparatus of the present invention may be employed as a means for etching the teeth by means of the laser beam prior to adhesive application, in lieu of an acid etch. In using the apparatus for this purpose, it might be desirable to place an adaptor guide tube into the guide tube 60 at end 62 in order to extend the guide tube 60 toward the tooth.

It will be appreciated, therefore, that the present invention provides a safe, effective and rapid means of removing ceramic orthodontic brackets without employing solely mechanical means or apparatus having elevated temperature elements in direct contact with the bracket.

While for purposes of ease of disclosure, reference has been made herein to an adaptation of a prior art mechanical device, it will be appreciated that other means wherein a single piece of apparatus may function as a means for both mechanically engaging the bracket so as to automatically position the laser guide tube discharge end in the desired place and laser beam delivery means may be employed.

Whereas particular embodiments of the invention have been described herein for purposes of illustration, it will be evident to those skilled in the art that numerous variation of the details may be made without departing from the invention as defined in the appended claims.

We claim:

1. Apparatus for removing a ceramic orthodontic bracket secured to a patient's tooth comprising
    a body portion having a handle and a head portion,
    bracket engaging means for engaging and removing the orthodontic bracket
    said bracket engaging and removing means being disposed within said head portion,
    operating means for opening and closing said bracket engaging and removing means whereby a force can be applied to the apparatus facilitating removal of the orthodontic brackets,
    laser generating means for generating a laser beam,
    guide means operatively associated with said body means and said laser generating means, for delivery of said laser beam from said laser generating means to the orthodontic bracket,
    said guide means having a discharge opening adjacent to said bracket engaging and removing means, and
    switch means for activating said laser generating means.

2. The apparatus of claim 1 including
    said guide means having at least a portion thereof secured to said body portion.

3. The apparatus of claim 2 including
    said guide means having at least a portion thereof passing through said head portion.

4. The apparatus of claim 3 including
    said guide means discharge opening being so disposed as to be in spaced relationship with respect to the orthodontic bracket during operation of said apparatus.

5. The apparatus of claim 4 including
    said guide means discharge opening being so positioned within said head portion as to be spaced about 0.5 to 2.0 mm from the orthodontic bracket when said laser generating means is activated.

6. The apparatus of claim 3 including
    said switch means being mounted on said body portion.

7. The apparatus of claim 6 including
    lens means disposed within said guide means for focusing said laser beam on the orthodontic bracket.

8. The apparatus of claim 3 including
    said laser generating means generating a laser beam of sufficient energy intensity to effect debonding of the orthodontic bracket in less than about five seconds.

9. The apparatus of claim 3 including
    said laser generating means generating a laser beam of predetermined duration responsive to operation of said switch means.

10. The apparatus of claim 2 including
    trigger means rotatably secured to said body portion for opening and closing said bracket engaging and removing means.

11. The apparatus of claim 1 including
    said bracket engaging and removing means being a pair of cooperating jaw means for engaging opposite sides of the orthodontic bracket.

12. A method of removing an orthodontic ceramic bracket from a patient's tooth comprising
    providing a body portion having a handle and head portion, bracket engaging means and laser beam guide means having a discharge end adjacent to said bracket engaging means,
    engaging said bracket with said bracket engaging means to position said discharge end in spaced relationship with respect to said bracket,
    applying and directing a laser beam of predetermined duration and energy intensity through said guide means and onto said bracket, and
    subsequently removing said bracket from said tooth.

13. The method of claim 12 including
    positioning said discharge end about 0.5 to 2.0 mm from said bracket.

14. The method of claim 13 including
    employing said laser beam to soften the adhesive securing said bracket to said tooth, whereby removal of said bracket as a unit may be effected.

15. The method of claim 14 including
    employing said method to remove ceramic brackets.

16. The method of claim 15 including focusing said laser beam on said bracket while resisting undesired exposure of said laser beam on portions of said teeth adjacent to said bracket.

17. The method of claim 14 including
directing said laser beam in a path generally perpendicular to the bracket.

18. The method of claim 17 including
subsequent to said laser beam application removing said bracket by moving said body member away from said tooth.

19. The method of claim 14 including
employing a laser beam wherein said bracket is not transparent to said laser beam and causing heat generated by said laser to pass to said adhesive by thermal conduction.

20. The method of claim 14 including
employing a laser beam wherein said bracket is transparent with respect to said laser beam and causing said beam to impinge directly on the adhesive securing said bracket to said tooth.

21. The method of claim 12 including
employing a laser beam of sufficient intensity to volatilize the adhesive securing said bracket to said tooth.

* * * * *